United States Patent
Dietz

(10) Patent No.: US 9,526,432 B2
(45) Date of Patent: Dec. 27, 2016

(54) ENHANCED SURFACE AND TIP FOR OBTAINING BIOELECTRICAL SIGNALS

(71) Applicant: Fresh Medical Laboratories, Inc., Salt Lake City, UT (US)

(72) Inventor: Phillip Dietz, Saint George, UT (US)

(73) Assignee: Fresh Medical Laboratories, Inc., Salt Lake City, UT (US)

( * ) Notice: Subject to any disclaimer, the term of this patent is extended or adjusted under 35 U.S.C. 154(b) by 80 days.

(21) Appl. No.: 14/269,248

(22) Filed: May 5, 2014

(65) Prior Publication Data

US 2015/0313488 A1 Nov. 5, 2015

(51) Int. Cl.
*A61B 5/0408* (2006.01)
*A61B 5/0478* (2006.01)
*A61B 5/0492* (2006.01)
*A61B 5/053* (2006.01)

(52) U.S. Cl.
CPC ........... *A61B 5/0408* (2013.01); *A61B 5/0478* (2013.01); *A61B 5/0492* (2013.01); *A61B 5/0532* (2013.01); *A61B 2562/0209* (2013.01)

(58) Field of Classification Search
CPC ... A61B 5/0492; A61B 5/0532; A61B 5/0408; A61B 5/0478; A61B 2562/0209
USPC ........................................ 600/372, 384, 547
See application file for complete search history.

(56) References Cited

U.S. PATENT DOCUMENTS

| | | | |
|---|---|---|---|
| 3,533,403 A * | 10/1970 | Woodson | A61B 5/0215 600/381 |
| 3,800,781 A * | 4/1974 | Zalucki | A61B 10/02 600/562 |
| 4,566,422 A | 1/1986 | Tadokoro et al. | |
| 4,616,660 A * | 10/1986 | Johns | A61N 1/36014 600/554 |
| 5,339,827 A | 8/1994 | Masopust | |
| 5,961,471 A * | 10/1999 | Nickson | A61B 5/0531 600/546 |
| 6,543,549 B1 | 4/2003 | Riedl et al. | |
| 7,536,220 B2 | 5/2009 | Horne | |
| 7,542,796 B2 | 6/2009 | Horne | |
| 7,937,139 B2 | 5/2011 | Horne | |
| 2004/0204658 A1 * | 10/2004 | Dietz | A61B 5/04025 600/547 |
| 2005/0014999 A1 | 1/2005 | Rahe-Meyer | |
| 2005/0015017 A1 | 1/2005 | Horne et al. | |
| 2005/0256512 A1 | 11/2005 | Del Rio et al. | |
| 2006/0178593 A1 | 8/2006 | Neubardt et al. | |
| 2007/0239061 A1 | 10/2007 | Carte | |
| 2010/0298863 A1 | 11/2010 | Hindinger et al. | |

* cited by examiner

*Primary Examiner* — Lee S Cohen
(74) *Attorney, Agent, or Firm* — Christopher L. Wight; Snow Christensen & Martineau

(57) ABSTRACT

The present invention is a device for providing an enhanced bioelectric sensing probe tip to facilitate locating and obtaining a bioelectric resistance value from a patient for therapeutic and/or diagnostic purpose. One embodiment of the present invention is a probe tip that comprises a uniform array of bristles that contacts a surface layer of a patient's skin to enable the bioelectric probe tip to locate and obtain a bioelectric resistance value from the patient. Another embodiment of the invention is to provide a probe tip cover that prevents foreign material from contaminating the probe tip and to assist in attaching the probe tip to a probe.

12 Claims, 3 Drawing Sheets

ENHANCED SURFACE AND TIP FOR OBTAINING BIOELECTRICAL SIGNALS

FIELD OF THE INVENTION

The present invention relates to obtaining bioelectric information. In particular, the present invention relates to systems and methods for providing and using an enhanced tip to facilitate locating and obtaining a bioelectric resistance value from a patient for assessment, therapeutic and/or diagnostic purposes.

BACKGROUND AND RELATED ART

Traditional medical science has long recognized certain electrical characteristics of humans and other living organisms. For example, the traditional medical community has recognized the electrical potentials generated by the human body in such forms as brain waves as detected by electroencephalographs (EEG), electrical impulses resulting from muscular heart activity as detected by electrocardiograms (EKG), and other electrical potentials measurable at other areas of the human body. While the relative levels of the electrical activity exhibit relatively small levels, such signals are nonetheless measurable and consistent.

In addition to measurable voltage levels, the human body and other mammalian organisms exhibit specific locations wherein the resistance value and the conductance value are relatively predictable for healthy individuals. The locations of anatomical dermal conductance points exhibit unique resistance values. Interestingly, the locations on the body exhibit a resistive reading of approximately 100,000 ohms and coincide with the body locations that correspond to the acupuncture points defined anciently by the Chinese. Indeed, Chinese medical practitioners were aware of the art of treating unfavorable health conditions through the use of needles that are used to pierce peripheral nerves to relieve pain. Electrical stimulation of these points provides similar results. Many acupuncture points are situated above major nerve trunks and have nerves within 0.5 centimeters of their location. Studies have indicated that many acupuncture points correspond to nerve innervations and trigger points. The acupuncture points are located under the skin (epidermis) and are accessed electrically through the skin either by the use of acupuncture needles or by using a probe tip pressed against the skin. As the outermost layer of epidermis (cornified layer) is less conductive, the probe tip mayor may not need a fluid or a type of electrode gel to enhance conductivity through the skin to the acupuncture point. Even so, the amount of pressure required to access the point can frequently invoke painful responses from the patient.

The representative acupuncture points and their relationship with organs and life systems of the human body have been characterized into more than 800 points that are organized into approximately 14 basic meridians. The measurable state of these acupuncture points reflects the condition of the related meridians and therefore the health of organs and other functions of the human body.

In the art of acupuncture, the acupuncture points are generally located at the extremity region of the hands and feet. As introduced above, the resistance value of healthy tissue at an acupuncture or conductance point is generally in the range of about 100,000 ohms. When such tissue is inflamed or infected, the conductivity is higher such that the measured resistance value appears lower than 100,000 ohms. Additionally, if the tissue is in a degenerative state, the conductivity is lower causing the resistance value to be higher.

Systems have been implemented to measure the resistance value at acupuncture points and present resistive values to a clinician for use in diagnosing a condition. However, the traditional systems have proven difficult to use since the precise location of the points is difficult to pinpoint, often requiring a probe tip to be placed on a specific angle in relation with the surface of the patient. Further, the differences in the characteristics of each patient and each point of a given patient can cause a practitioner to obtain inaccurate and/or unrepeatable readings. Moreover, current technologies have caused pain and/or discomfort to patients.

In some systems, a first device is used to locate the points and a second device is brought in contact with the point to perform the electro-dermal screening. While this technique is available, employing multiple devices introduces a potential for clinical error. Accordingly, other systems have been made available that include both a point finding function and an electro-dermal screening function. However, in every case the system used proves difficult to locate the points on the patient. And, the electro-dermal screening is compromised when the system does not accurately determine the points.

Thus, while techniques currently exist that are used to locate a point on a patient, challenges still exist, such as inaccurate readings, unrepeatable readings, pain, discomfort, and the like. Accordingly, it would be an improvement in the art to augment or even replace current techniques with other techniques.

SUMMARY OF THE INVENTION

The present invention relates to obtaining bioelectric information. In particular, the present invention relates to systems and methods for providing and using an enhanced surface to facilitate locating and obtaining a bioelectric resistance value from a patient for assessment, therapeutic and/or diagnostic purposes.

Implementation of the present invention takes place in association with an abrasive bristly conductive probe tip that is used to obtain a bioelectric value from a patient. The uniform array of abrasive bristles which have a conductive surface are able to simultaneously contact and/or puncture a surface layer of a patient's skin (e.g., the cornified layer of the epidermis) to enable and facilitate locating and obtaining a bioelectric resistance value from the patient.

In one implementation, the tip is covered with a clean protective cover. The cover protects the probe tip from damage and foreign contaminates. In addition, the cover provides a grip for the user to easily handle the probe tip. The cover also gives a mechanical advantage for the user to connect the tip to a probe.

These and other features and advantages of the present invention will be set forth or will become more fully apparent in the description that follows and in the appended claims. Those skilled in the art will appreciate that the methods and processes can be used in association with a variety of different bioelectric sensing devices, including patches, clips, and the like to provide an enhanced bioelectric sensing surface. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

Figure 1:
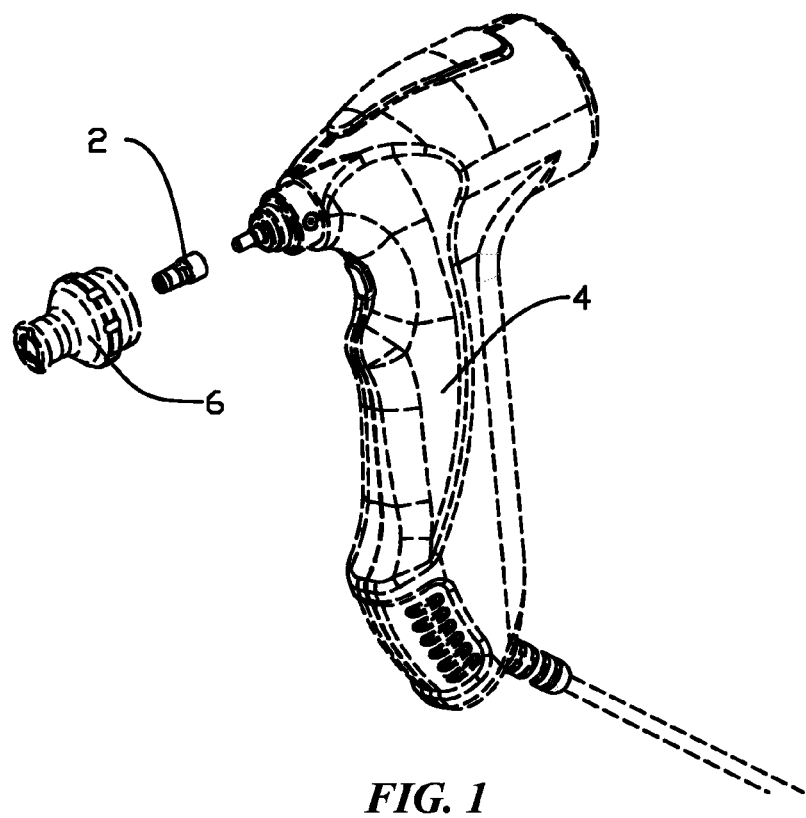
FIG. 1 is a side elevation view of the tip with the broken line showing of environmental association matter being for illustrative purposes only and forming no part of the claimed device.

| Drawing -Reference Numbers | |
|---|---|
| 2 | Probe tip |
| 4 | Probe |
| 6 | Isolation hood |
| 8 | Bristle |
| 12 | seal rim |
| 14 | Cover |
| 18 | Probe shaft |
| 20 | Distal end |
| 22 | Proximal end |
| 24 | Receiving cavity |
| 26 | Grip |
| 28 | Screw threads |
| 30 | Plain surface |
| 32 | Level surface |

DETAILED DESCRIPTION OF THE INVENTION

The present invention relates to obtaining bioelectric information. In particular, the present invention relates to systems and methods for providing and using an enhanced surface that is used to facilitate locating and obtaining a bioelectric values from a patient for assessment, therapeutic and/or diagnostic purposes.

In the flowing description of the invention, certain terminology is used for the purpose of reference only, and is not intend to be limiting. Terms such as "upper", "lower", "above", and "below," refer to directions in the drawings to which reference is made. Terms such as "inwards" and "outward" refer to directions towards and away from, respectively, the geometric center of the component described. Terms such as "side", "top", "bottom," "horizontal," "with in," "inside," and "vertical," describe the orientation of portions of the component within a consistent but arbitrary frame of reference which is made clear by reference to the text and the associated drawings describing the component under discussion. Such terminology includes words specifically mentioned above, derivatives thereof, and words of similar import.

Embodiments of the present invention take place in association with an abrasive bristly conductive probe tip that is used to obtain a bioelectric value. Some embodiments embrace a bioelectric probe using the probe tip that includes a device for measuring and recording the bioelectric value. The abrasive bristly conductive probe tip includes an array of uniform bristles such that a variety of the bristles are able to simultaneously contact and/or puncture the cornified layer of a patient's epidermis to enable at least one bristle to be in contact with the acupuncture point and to obtain a bioelectric resistance value from the patient.

In the disclosure and in the claims the term "abrasive bristly probe tip" shall refer to an abrasive construction of a plurality of bristles, wherein at least one of the bristles is able to locate and/or obtain a bioelectric value of a patient. An example of an abrasive bristly conductive probe tip includes one or more materials and/or coatings such as: brass, brass alloy or pleated brass.

In accordance with at least some embodiments of the present invention, a patient may undergo bioelectric therapy corresponding to a condition diagnosed at an anatomical dermal conductance point. The various anatomical dermal conductance points are typically located throughout a patient's hands and feet. The dermal conductance points or acupuncture points aid the clinician in assessing and/or diagnosing a patient's condition and pinpointing a particular disorder.

In accordance with embodiments of the present invention, a patent's condition may be assessed and/or diagnosed using a device or equipment capable of measuring the resistance or likewise the conductance at anatomical dermal conductance points located throughout the hands and feet of the patient.

Thus, while embodiments of the present invention embrace a variety of different systems having an abrasive bristly conductive surface, the following relates to a representative system that includes a bioelectric probe having a probe tip. The probe tip is placed on an anatomical dermal conductance point. The conductance value is measured between the probe and a ground bar, and is displayed on a conductance monitor or other output for evaluation by a clinician or practitioner. If the conductance value at a particular conductance point on the patient denotes an imbalance, the clinician may investigate the biological system meridian that corresponds to the conductance point presenting the imbalanced reading. Conversely, when a particular conductance point displays a balanced reading, the clinician thereafter measures the conductance at various other conductance points to properly assess and/or diagnose the condition of the patient.

Upon evaluating the condition of the patient, such as an organ disorder or a biological system abnormality, the clinician selects a possible remedy for such a condition. Remedies may include providing a homeopathic remedy or a digital sequence that is known to exhibit a particular reaction on an individual. An electromagnetic energy source generates a frequency coded electromagnetic signal containing the digital sequence, which is broadcast or projected upon the patient. The frequency coded electromagnetic signal may take the form of several electromagnetic types, such as radio frequency (RF) signals, infrared (IR) signals or other electromagnetic projections.

As illustrated in FIG. 1, a probe tip 2 connects to a probe 4. The probe tip 2 includes screw threads 28 located within the probe tip 2. The screw threads 28 are designed to mate with a complementary thread (not shown) on the probe 4, such that the probe tip 2 is securely fastened to the probe 4, but easily removed from the probe tip 2. Those skilled in the art will recognize that different methods such as friction, smaller thread or quick releasing mechanisms may attach the probe tip 2 to the probe 4.

Figure 2:
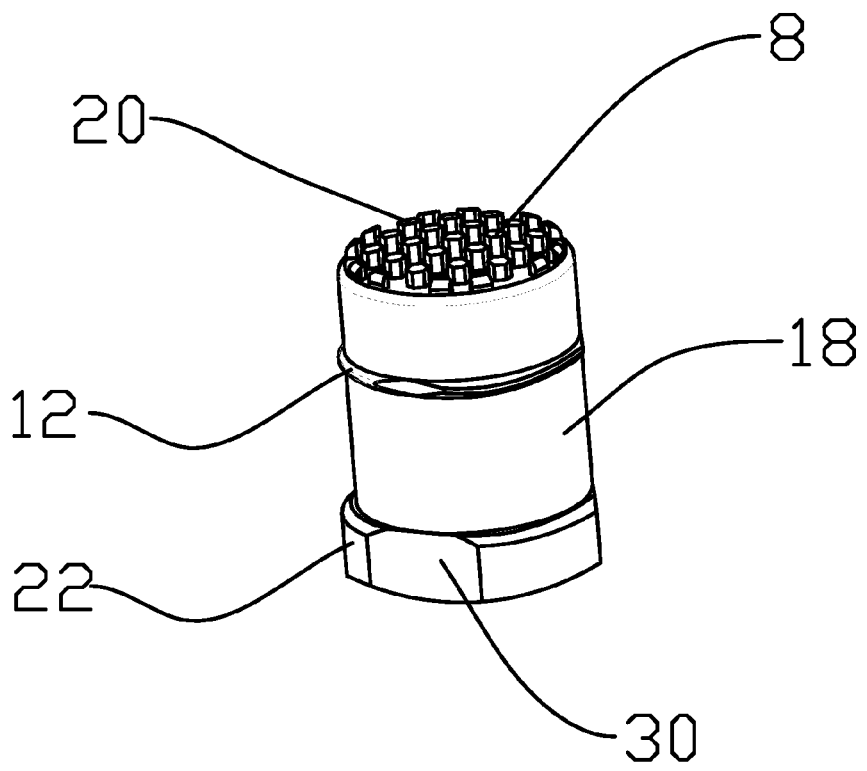
FIG. 2 illustrates another representative a side view of the probe tip showing the uniform array of the bristles and the plain surface.

FIG. 2 illustrates a probe tip 2 that includes a distal end 20 and a proximal end 22. The distal end 20 is convex and may be wider than the proximal end 22. The convex nature of distal end 20 reduces the need for a precise location and/or a precise angle in relation with the dermal surface layer to locate and obtain the bioelectric resistance value. As described above, the proximal end 22 is configured for electronic coupling to a mechanism for reading the bioelectrical resistance value such as a probe 4 shown in FIG. 1. Located between the distal end 20 and the proximal end 22 is a probe shaft 18. The probe shaft 18 includes a seal rim 12 which is discussed below.

The distal end 20 includes an array of bristles 8. The bristles 8 form a uniform array pattern across the face of the distal end 20. Those skilled in the art will appreciate that while the bristles 8 have been illustrated in a circular configuration, other embodiments embrace other non-circular configurations. Further, as provided herein, at least some of the embodiments of the present invention include a low density of bristles 8 having a few multiple points to enable an enhanced bioelectric sensing surface.

Each bristle 8 is a hexagon shape. However, those skilled in the art will recognize that other geometric shapes may form the individual bristles 8. The height of each bristle 8 ranges from 0.001 millimeters to 1 millimeters. In some embodiments, the bristles 8 are random in length. In other embodiments, the bristles are more uniform. Further, in some embodiments one or more of the bristles puncture the cornified layer of the epidermis to obtain the bioelectric value(s). In other embodiments, the bristles 8 do not puncture the cornified layer and may optionally be used in combination with a material, such as water, to enhance obtaining the bioelectric value(s).

The preferred material of the bristle 8 is brass, a brass alloy or brass plated metal. In practice, the entire probe tip 2 will be made of the same material as the bristles 8. The bristles 8 may be coupled, machined, etched, molded and/or otherwise manufactured to the probe tip 2 in a variety of manners.

Figure 3:
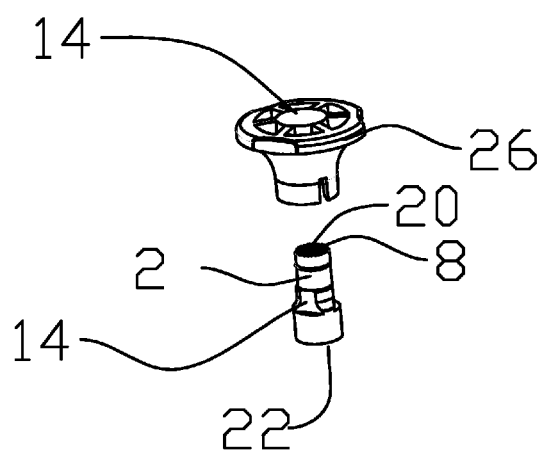
FIG. 3 illustrates an exploded side view of the probe tip and cover.
Figure 4:
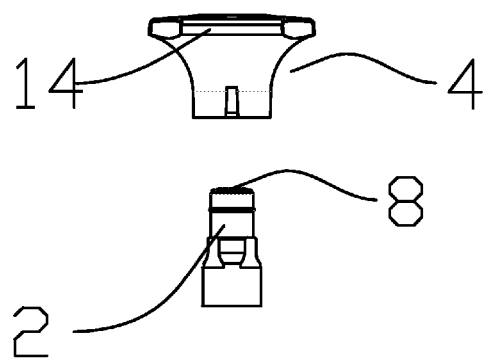
FIG. 4 illustrates another a side view of the probe tip and cover.
Figure 5:
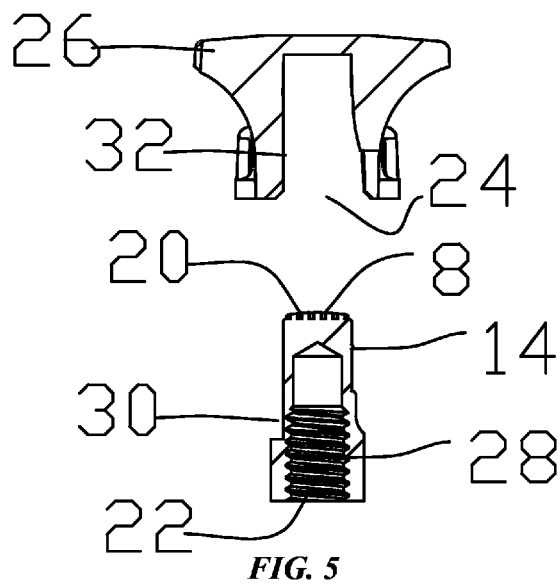
FIG. 5 illustrates an exploded cross section view of the probe tip and cover.
Figure 6:
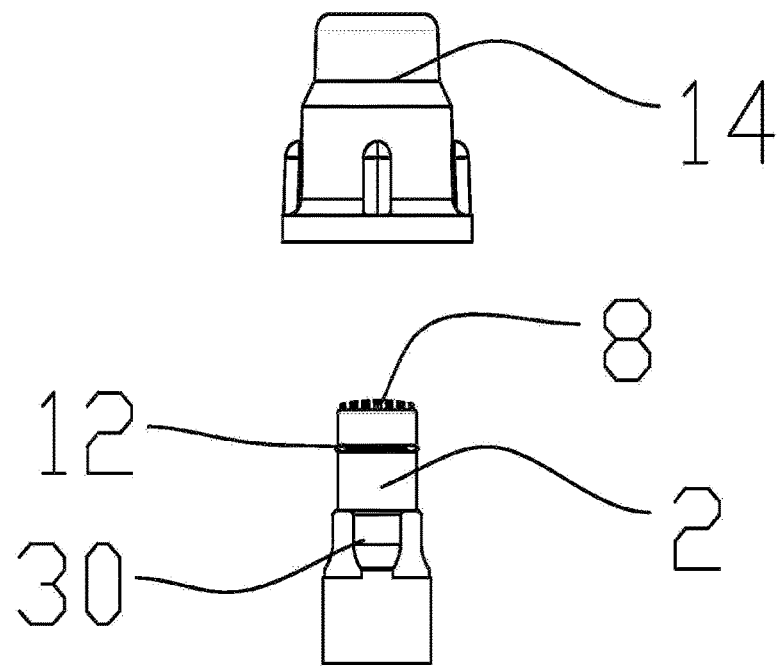
FIG. 6 illustrates another configuration of the cover and the tip.
Figure 7:
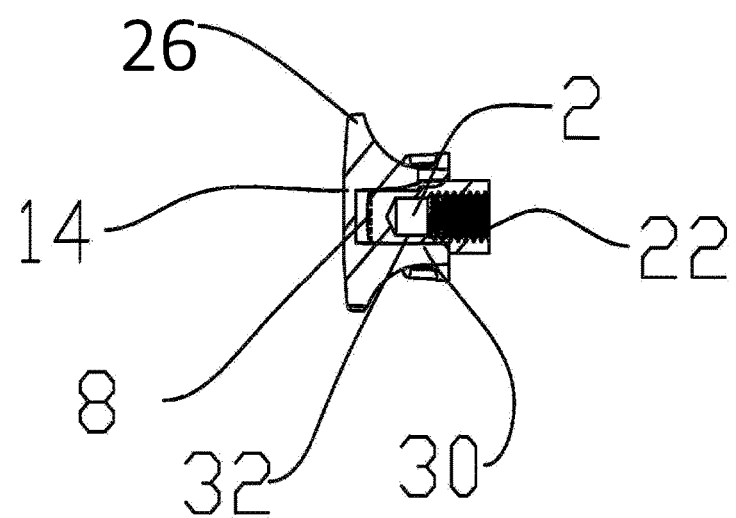
FIG. 7 illustrates a cross section view of the probe tip and cover.

As illustrated in FIG. 7, the probe tip 2 is protected by a cover 14. The cover 14 includes a receiving cavity 24 and a grip 26. During storage of the probe tip 2, the probe tip 2 is placed within the receiving cavity 24. In addition, the cover 14 keeps foreign contaminates from contacting the bristles 8, thus allowing the bristles 8 to remain sterile. The cover 14 is made from any non-conductive material such as plastic or nylon. Accordingly, FIGS. 3-5 provide additional representative cover 14 configurations for use in association with the present invention. Those skilled in the art will appreciate that the cover 14 embrace a variety of other types of configurations.

As shown in FIG. 2, the seal rim 12 is located near the mid-section of the probe shaft 18. The diameter of the seal rim 12 is great than the diameter of the probe shaft 18. Thus, the seal rim 12 extends out from the probe shaft 18. However, the diameter of the seal rim 12 is slightly larger than the diameter of the receiving cavity 24. When probe tip 2 is placed inside the receiving cavity 24, the seal rim 12 pushes against the sides of the receiving cavity 24, creating resistance between the probe tip 2 and cover 14 such that a deliberate force is required to remove probe tip 2.

Located at the proximal end 22 of the probe tip 2 is at least one plain surface 30. A corresponding level surface 32 is located on the receiving cavity 24 of the cover 14. The plain surface 30 and level surface 32 are similar in size and shape. When probe tip 2 is placed inside the receiving cavity 24, the plain surface 30 and the level surface 32 connect. When the user screws the probe tip 2 onto a probe 4, the user applies a torque force to the cover 14. The cover 14 transfers the torque force to the probe tip 2 to allow the tip to screw onto the probe 4. The increased surface area created by the plain surface 30 and the level surface 30, allows the cover 14 to transfer a great torqueing force to the probe tip 2. In practice, at least three plain surfaces 30 and level surfaces 32 will be located on the probe tip 2 and receiving cavity 24.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed:

1. A device for obtaining an electrical signal from a patient at the patient's skin, said device comprising:
   (a) a probe tip having a distal end and a proximal end;
   (b) the proximal end having a means for releaseably attaching to a probe;
   (c) the distal end having an array of bristles comprising a sensing surface at a tip, wherein the tip of the bristles have a hexagonal shape;
   wherein the bristles are configured such that a plurality of the bristles simultaneously contact a dermal surface layer of a patient to enable the sensing surface to locate and obtain a bioelectric resistance value from the patient.

2. The device of claim 1, wherein the probe tip is made of brass, brass alloy or brass plated material.

3. The device of claim 1, wherein the array of bristles form a uniformed pattern.

4. The device of claim 1, wherein the array of bristles height varies from 0.01 millimeters to 1 millimeters.

5. The device of claim 1, the means for attaching the probe tip to the probe is by a threaded screw threads.

6. A device for obtaining an electrical signal from a patient at the patient's skin, said device comprising:
   (a) a probe tip having a distal end and a proximal end;
   (b) the proximal end having a means for releaseably attaching to a probe;
   (c) the distal end having an array of bristles comprising a sensing surface at a tip, wherein the tip of the bristles have a hexagonal shape;
   (d) a cover comprising a receiving cavity and a grip;
   wherein the bristles are configured such that a plurality of the bristles simultaneously contact a dermal surface layer of a patient to enable the sensing surface to locate and obtain a bioelectric resistance value from the patient;
   wherein the probe tip is placed into the receiving cavity for storage.

7. The device of claim 6, wherein the cover is made of a non-conductive material.

8. The device of claim 6, the probe tip includes a plane surface near the proximal end and the receiving cavity includes a level surface that is similar in size and shape as the plane surface;
   wherein when a torquing force is applied to the grip, the torquing force is transferred to the probe tip.

9. The device of claim 6, the probe tip includes a seal rim; wherein, the diameter of the seal rim is slightly larger than the diameter of the receiving cavity.

10. A method for obtaining an electrical signal from a patient at the patient's skin:
   (a) selecting a device comprising:
      (i) a probe tip having a distal end and a proximal end;
      (ii) the proximal end having a means for attaching to a probe;
      (ii) the distal end having an array of bristles comprising a sensing surface at a tip, wherein the tip of the bristles have a hexagonal shape;
      wherein the bristles are configured such that a plurality of the bristles simultaneously contact a dermal surface layer of a patient to enable the sensing surface to locate and obtain a bioelectric resistance value from the patient
   (b) placing the device against a dermal surface layer of the patient.

11. The method of claim 10, the device includes a cover, the cover having a receiving cavity and a grip; wherein placing the probe tip in the receiving cavity to protect the probe tip during storage.

12. The method of claim 11, wherein the probe tip includes a plane surface near the proximal end and the receiving cavity includes a level surface that is similar in size and shape as the plane surface; wherein a torquing force is applied to the grip, and the torquing force is transferred to the probe tip.

* * * * *